(12) United States Patent
Steinhardt et al.

(10) Patent No.: US 7,553,328 B2
(45) Date of Patent: Jun. 30, 2009

(54) OSSICLE PROSTHESIS

(75) Inventors: Uwe Steinhardt, Hirrlingen (DE); Heinz Kurz, Dusslingen (DE)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 405 days.

(21) Appl. No.: 10/579,927

(22) PCT Filed: Dec. 7, 2005

(86) PCT No.: PCT/EP2005/013077

§ 371 (c)(1),
(2), (4) Date: May 19, 2006

(87) PCT Pub. No.: WO2006/094543

PCT Pub. Date: Sep. 14, 2006

(65) Prior Publication Data

US 2008/0195201 A1 Aug. 14, 2008

(30) Foreign Application Priority Data

Mar. 9, 2005 (DE) .................. 10 2005 010 705

(51) Int. Cl.
*A61F 2/18* (2006.01)
(52) U.S. Cl. ........................................ 623/10
(58) Field of Classification Search ............ 623/10; 600/25
See application file for complete search history.

(56) References Cited

U.S. PATENT DOCUMENTS 6,168,625 B1  1/2001  Prescott
6,387,128 B1  5/2002  Kurz et al.
6,579,317 B2  6/2003  Kurz
7,074,222 B2 * 7/2006  Westerkull .................. 606/312
2004/0148025 A1 * 7/2004  Schneider et al. ............ 623/10
2005/0027357 A1  2/2005  Steinhardt et al.
2005/0107869 A1 * 5/2005  Sirhan et al. ............... 623/1.42
2005/0165481 A1 * 7/2005  Steinhardt et al. ............ 623/10
2005/0267600 A1 * 12/2005  Haberman et al. ........... 623/38
2007/0048708 A1 * 3/2007  Lee ........................... 434/236

FOREIGN PATENT DOCUMENTS

DE  299 04 770   7/1999
DE  100 45 158   3/2002
DE  203 10 609  10/2003
EP  0 998 884    5/2000
EP  1 181 907    2/2002

* cited by examiner

*Primary Examiner*—Thomas J Sweet
*Assistant Examiner*—Yashita Sharma
(74) *Attorney, Agent, or Firm*—Michael J. Striker

(57) ABSTRACT

An ossicle prosthesis (10) includes a first securing element (11) and a second securing element (12), the second securing element connected to a member of the ossicle chain. The ossicle chain ends at the first securing element in a ball joint, which includes two struts (13, 13') solidly connected to the first securing element (11). The two struts enclose a gaplike space, in which a ball (14) is pivotably supported in two recesses (15), the ball (14) being part of an elongated shaft (16) that connects the first and second securing elements and includes many balls (14, 14', 14") adjacent to one another. The elongated shaft is displaceable through the gaplike space between the two struts and through a perforation (17) in the first securing element, where one of the balls snaps between the respective recesses. The gaplike space can be made narrower between the two struts (13, 13') of the ball joint for fixation of the shaft (16) after the desired length has been adjusted.

16 Claims, 2 Drawing Sheets

OSSICLE PROSTHESIS

Figure 1:
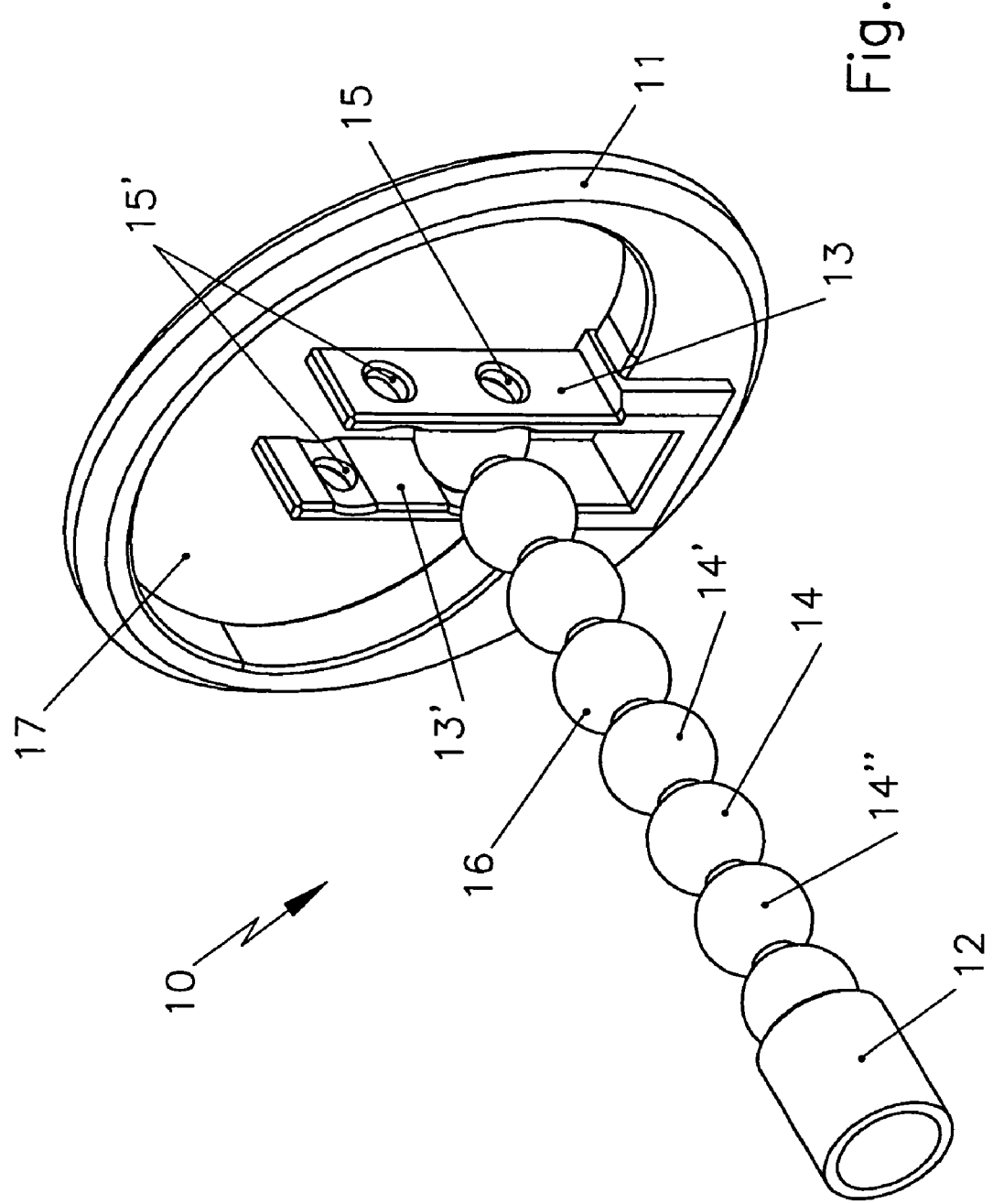

The invention relates to an ossicle prosthesis, which replaces or spans at least one member of the chain of human auditory ossicles, in which the ossicle prosthesis, on both of its ends, has a first securing element and a second securing element for mechanical connection to a member of the ossicle chain, to the eardrum or to the inner ear, and between the two securing elements has a ball joint, which includes two struts, which are solidly joined to the first securing element, extend parallel or at an angle to one another, and between them enclose a gaplike space, in which a ball is pivotably supported in two recesses in the struts, and the ball is part of an elongated shaft which connects the two securing elements to one another.

One such device is known from German Utility Model DE 203 10 609 U1 or from European Patent Disclosure EP 1 181 907 B1.

Ossicle prostheses are used, when the ossicles of the human middle ear are entirely or partly absent or damaged, to transmit the sound from the eardrum to the inner ear. The ossicle prosthesis has two ends, and depending on the specific given conditions, one end of their ossicle prosthesis is secured, for instance by means of a head plate, to the extension of the incus in the human ossicle chain, and the other end of the ossicle prosthesis is secured for instance to the stapes of the human ossicle chain, or is plunged directly into the inner ear. Often with the known ossicle prostheses, conducting sound between the eardrum and the inner ear is made possible only to a limited extent, since these prostheses are only extremely limitedly capable of replacing the natural anatomical features of the ossicle chain.

Once the prosthesis has been surgically placed in the middle ear and the eardrum has been closed again, the so-called healing phase begins. During this time, scars form, and these engender unpredictable forces, which can cause the prosthesis to shift out of its local position. If there is a rigid connection between the head plate and the shaft, increased pressure peaks can occur between the edge of the head plate and the eardrum, or between the transplant between the eardrum and the head plate. These peaks can be so high that they would cause penetration of the eardrum. For this reason it is very helpful if the head plate postoperatively conforms automatically to the position of the eardrum. Since moreover the given anatomical conditions of the ear, such as the location, shape and size of the stapes, incus, malleus, and eardrum, do vary, it is highly advantageous if ossicle prostheses are not embodied rigidly but instead have a certain flexibility or variability. To achieve this flexibility/variability, various securing and coupling devices for auditory ossicles are known that have elastic parts and/or joints. One such articulated connection between a securing element, which can be mounted on the base of the stapes, and the elongated shaft is described in the aforementioned disclosure EP 1 181 907 B1 and is sold by the present Applicant under the tradename "Ball-Joint".

Because of the anatomically and genetically dictated range of variation, in tympanoplasty, middle ear prostheses of different lengths are needed for reconstructing the ossicle chain in otology. Unfortunately, at present it is not possible before an operation to know what the actual length needed will be. It is therefore necessary either to have prostheses of various lengths on hand, which is expensive, or the prosthesis must be variable in its length, so that immediately before its implantation it can be adapted individually to the particular patient. Since the relative location of the ossicle prosthesis with respect to the eardrum also differs somewhat in each person, before the prosthesis is inserted the middle ear must be precisely measured with regard to the location of the securing elements. The required length of the shaft, however, cannot be determined until during the operation, so that for each operation, either a set of prostheses of different lengths, or one prosthesis with a variable shaft length, must be made available.

One favorable way of cutting the shaft to the individual length with little effort or expense for the shaft and thus more economically is described in European Patent Disclosure EP 0 998 884 B1. Such ossicle prostheses are sold by the present Applicant under the tradename "VARIO". In these known prostheses, the shaft protrudes through a through bore in the first securing element, which is embodied as a head plate. The shaft can be displaced axially through the through bore in such a way that it protrudes on the outside of the head plate and can be cut to length there, and the through bore can be narrowed afterward, in order to fix the shaft at the desired point. A similar technique for cutting to length is also described in U.S. Pat. No. 6,168,625 B1 and the associated German Patent Disclosure DE 100 45 158 A1; in these disclosures, the shaft has many notches along its axis, which are meant to serve as rated breaking points for unproblematically cutting the shaft to length later during the operation. The thus-created wavy shaft is intended to produce increased friction within a receiving part. However, postoperative automatic compensation for hydrostatic forces engaging the eardrum cannot be done here, because if for no other reason the receiving part, together with the portion surrounded by it of the wavy shaft, does not form a ball joint.

By comparison, it is the object of the present invention to improve a generic device of the type described at the outset such that both a pivot point that can be produced with little effort and expense, for attaining a requisite postoperative flexibility and variability of the prosthesis, and a shaft that can be adjusted to an individual length by simple technical means and therefore also economically, are present yet without requiring prostheses of different lengths to be kept on hand at high expense and without requiring the use of complicated special tools for individually adjusting the length during the operative implantation of the prosthesis.

According to the invention, this object is attained in a way that is both surprisingly simple and effective, in that the elongated shaft includes many balls adjoining one another, of which one is the ball in the ball joint, that the elongated shaft is displaceable through the gaplike space between the two struts of the ball joint, in a direction perpendicular to the struts and toward or away from the first securing element and through a perforation in the first securing element, and one each of the balls snaps in a snapped-in position between the recesses of the struts, so that a desired length of the shaft modulus adjusts the spacing of the balls from one another, and the part of the shaft protruding through and past the first securing element can be cut to length, and that the gaplike space between the two struts of the ball joint can be made narrower for fixation of the shaft after the desired length has been adjusted.

In the ossicle prosthesis of the invention, the shaft and the ball joint are accordingly not separate parts of the prosthesis, as in the case of the prosthesis of EP 1 181 907 B1, but instead, because of the construction of the shaft as a "ball chain", the shaft itself acts as part of the ball joint. As a result, in a wonderfully simple way, the advantages of the "Ball-Joint" prosthesis described above are combined with those of the "VARIO" prosthesis of EP 0 998 884 B1, and because the joint ball and shaft are fused into a single component, the entire device can be made even more compact and thus more inexpensively. The automatic postoperative adjustment of force in the bearing of the ball seat is also very important. On the one hand, this adjustment must not be overly great, because then no motion occurs; on the other, it must not be too slight, because that could lead to defective signal transmission. An optimal solution to this problem is also furnished by the device of the invention.

An embodiment of the ossicle prosthesis of the invention that can be produced in especially compact and therefore economical form is one in which the two struts of the ball joint are embodied integrally with the first securing element.

A further preferred embodiment of the invention includes an ossicle prosthesis, in which each of the two struts of the ball joint has at least one and preferably plurality of recesses, located side by side, for receiving a ball of the elongated shaft, and two recesses of the two struts are always diametrically opposite one another. As a result, during the operation, the location of the shaft in relation to the first securing element, which as a rule will be embodied as a head plate, is also variable within certain limits. In this way, in particular, a force adjustment in the bearing of the ball joint can be done, so that postoperatively, the head plate conforms in its position automatically and optimally to the eardrum.

An advantageous refinement of this embodiment provides that the recesses have the shape of round holes.

In an alternative embodiment of the invention, it is provided that each of the two struts of the ball joint has at least one oblong-slot-shaped recess for receiving a ball of the elongated shaft displaceably in the longitudinal direction of the oblong hole, and two recesses of the two struts are always diametrically opposite one another. With this provision as well, crosswise shifting of the elongated shaft in a direction transverse to its axis can be realized between the two struts, in order to attain an optimal adaptation of position.

An embodiment of the ossicle prosthesis of the invention that is especially simple and economical to produce is one in which the balls of the elongated shaft each have the same outer diameter and are located equidistantly along the axis of the shaft. This also facilitates manipulation as the shaft is cut to length during the surgical implantation.

An embodiment in which the elongated shaft includes a rod element, onto which balls provided with through bores and then fixed on the rod element are slipped, is also advantageous for manufacture.

It is especially favorable for manufacturing this embodiment if the balls are welded to the rod element, preferably by means of laser welding.

An advantageous refinement of this embodiment provides that the through bores of the balls are also produced by means of lasers.

A refinement of the above-described embodiment of the device of the invention in which the rod element is made from a flexible material is very particularly preferred; this considerably improves the above-described postoperative, automatic, optimal adaptation of the position of the implant.

Other preferred embodiments of the device of the invention are distinguished in that the securing elements are embodied in plate-, bell-, or ram-shaped form or as a clip. In principle, still other embodiments of the securing elements are conceivable, but the forms described above have proved themselves especially well in practice.

Depending on a patient's individual defect that is to be eliminated or at least mitigated in its effects by the use of the ossicle prosthesis of the invention, the construction of the prosthesis is designed to suit. In many embodiments, the first securing element can for instance include a head plate embodied for contact with the eardrum.

Other features may provide that the prosthesis is secured on one side to the incus extension and on the other to the stapes or is plunged directly into the inner ear.

In still other embodiments of the invention, the prosthesis is secured on one side to the handle of the malleus and on the other to the incus or to the stapes, or is plunged directly into the inner ear.

In this connection, a refinement in which the ossicle prosthesis is located at the end point of the malleus (or umbo) or directly next to it is advantageous, because then the greatest leverage is attained for mechanically transmitting the sound by means of motions in the artificial or natural ossicle chain.

A further especially preferred embodiment of the device of the invention is distinguished in that the ossicle prosthesis is coupled on one end directly to the inner ear, particularly via a piston, by means of opening up the cochlea (cochleotomy).

An embodiment of the device of the invention is preferred in which the prosthesis or parts thereof are made from biocompatible plastics, in particular silicone, or fiber-reinforced materials. This can prevent postoperative rejection reactions in most cases.

The ossicle prosthesis of the invention or parts thereof can be made from titanium and/or gold and/or tantalum and/or an alloy of these metals.

Embodiments of the invention in which the prosthesis or parts thereof are made from a material with shape memory (memory effect), in particular Nitinol, are advantageous with a view to the aforementioned postoperative adaptation of position.

An embodiment of the device of the invention in which the distribution in terms of mass of the individual parts of the prosthesis is calculated as a frequency of a desired, predeterminable frequency response of the conduction of sound in the middle ear, is very particularly preferred. With it, tuning of the sound propagation properties can be achieved to a certain extent by means of an individually designed ossicle prosthesis.

This kind of tuning effect can be attained in special embodiments, for instance in that at least one additional mass is secured to a part of the ossicle chain or the prosthesis as a function of a desired, predeterminable frequency response of the conduction of sound in the middle ear.

In advantageous refinements of these embodiments, the additional mass is secured by means of a clip to a part of the ossicle chain or of the prosthesis.

A further embodiment of the invention, finally, is distinguished in that the prosthesis is connected to an active vibrating part of an active, in particular implantable, hearing aid. Thus even extensive hearing damage over wide ranges can be eliminated or at least substantially mitigated in its effects by using modern electronics.

Further characteristics and advantages of the invention will become apparent from the ensuing detailed description of exemplary embodiments of the invention in conjunction with the drawing figures, which show details essential to the invention, and from the claims. The individual characteristics can each be realized individually or a plurality of them in arbitrary combinations in variations of the invention can be attained.

In the schematic drawing, exemplary embodiments of the invention are shown, which are explained in further detail in the ensuing description.

Figure 2:
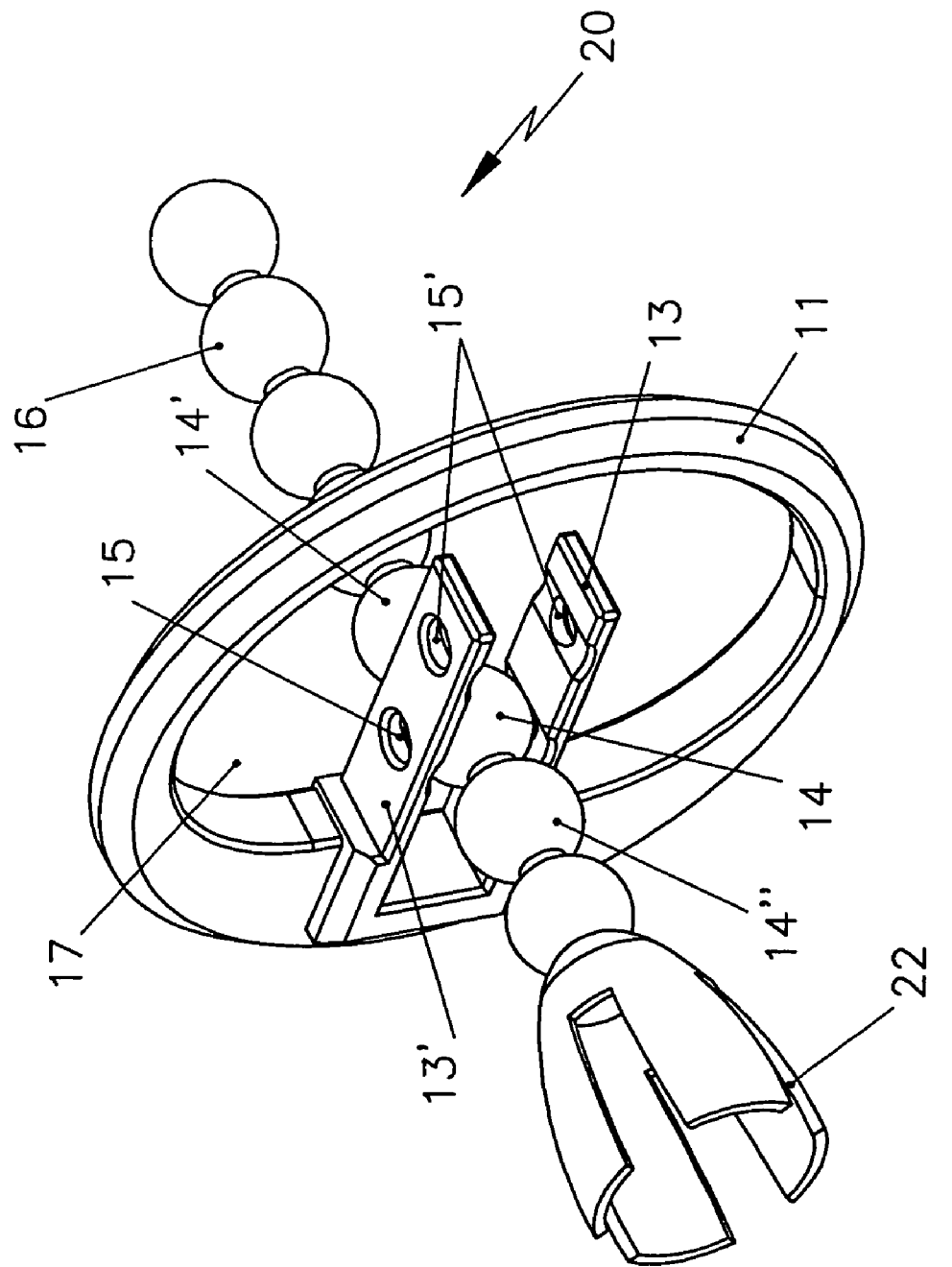

Shown are:

FIG. 1, a schematic three-dimensional view of one embodiment according to the invention, having a first securing element embodied as a head plate and a ram-shaped second securing element on the other end of the elongated shaft, the elongated shaft with the balls not yet having been inserted into the gaplike space between the two struts; and FIG. 2, a further embodiment, with a second securing element that is bell-shaped instead of ram-shaped, and in which the elongated shaft with one ball has already snapped in the snapped-in position between the recesses of the struts.

The ossicle prosthesis 10 shown in FIG. 1 has a first securing element 11, which is embodied in the form of a head plate for contact with the eardrum. On the other end of the ossicle prosthesis 10, a second securing element 12 is provided, which in the present exemplary embodiment is embodied in ram-shaped form. The first securing element 11 includes two diametrically opposed struts 13, 13', which between them enclose a gaplike space and which each have two recesses 15, 15', located side by side and in the present exemplary embodiment embodied as round holes. An elongated shaft 16 is thrust into this gaplike space and includes a plurality of balls 14, 14', 14", adjacent to one another, and the second securing element 12 is mounted on the end of this shaft facing away from the first securing element 11.

For adjusting the desired shaft length, the shaft 16 is thrust in the axial direction through the gap between the two struts 13, 13' and a perforation 17, provided for this purpose, in the first securing element 11 until, in the desired position, a ball 14 snaps into place between the two recesses 15. The two struts 13, 13', the ball 14, and the two recesses 15 then together form a ball joint.

This situation is shown in FIG. 2, but here the second securing element 22 of the ossicle prosthesis 20 is embodied as bell-shaped. As soon as the ball 14 has snapped into the two diametrically opposed recesses 15 in the struts 13, 13', the shaft 16 can be cut to the desired final length between the snapped-in ball 14 and the balls 14' adjacent to it, for instance by means of cutting tongs or some other suitable microinstrument.

The relative position of the shaft 16 with respect to the first securing element 11 can be varied by positioning the ball 14 not between the two recesses 15, but offset in parallel between the two recesses 15' of the struts 13, 13'.

The invention claimed is:

1. An ossicle prosthesis (10; 20), which replaces or spans at least one member of a human ossicle chain, in which the ossicle prosthesis (10; 20) includes a first securing element (11) on one end and a second securing element (12; 22) on its other end, the second securing element adapted for mechanical connection to a member of the ossicle chain, to the eardrum or to the inner ear, wherein between the two securing elements (11, 12; 22) is a ball joint, which includes two struts (13, 13') that are solidly joined to the first securing element (11), and extend parallel or at an angle to one another enclosing a gaplike space in which a ball (14) is pivotably supported in two recesses (15) in the struts (13, 13'), and which ball (14) is part of an elongated shaft (16) that connects the two securing elements (11, 12; 22) to one another,
wherein
the elongated shaft (16) further includes a plurality of balls (14, 14', 14") adjoining one another, of which one ball (14) is in the ball joint, and,
is displaceable through the gaplike space between the two struts (13, 13') of the ball joint, in a direction perpendicular to the struts (13, 13') extending towards or away from the first securing element (11), through a perforation (17) in the first securing element (11), wherein each of the balls (14, 14', 14") snaps in a snapped-in position between the recesses (15) of the struts (13, 13'), so that a desired length of the shaft (16) modulus adjusts the spacing of the balls (14, 14', 14") from one another, and the part of the shaft (16) protruding through and past the first securing element (11) can be cut to length;
and wherein the gaplike space between the two struts (13, 13') of the ball joint can be made narrower for fixation of the shaft (16) after the desired length has been adjusted.

2. The ossicle prosthesis as defined by claim 1, wherein the two struts (13, 13') of the ball joint are embodied integrally with the first securing element (11).

3. The ossicle prosthesis as defined by claim 1, wherein each of the two struts (13, 13') of the ball joint has at least one recess for receiving a ball (14) of the elongated shaft (16).

4. The ossicle prosthesis as defined by claim 3, wherein the recesses (15, 15') have the shape of round holes.

5. The ossicle prosthesis as defined by claim 1, wherein each of the two struts of the ball joint has at least one oblong-slot-shaped recess for receiving a ball (14) of the elongated shaft (16) displaceably in the longitudinal direction of the oblong hole, and wherein two recesses of the two struts are arranged diametrically opposite one another.

6. The ossicle prosthesis as defined by claim 1, wherein the balls (14, 14', 14") of the elongated shaft (16) each have the same outer diameter and are located equidistantly along the axis of the shaft (16).

7. The ossicle prosthesis as defined by claim 1, wherein the elongated shaft (16) includes a rod element, and wherein balls (14, 14', 14") are provided with through bores through which they are slipped and then fixed on the rod element.

8. The ossicle prosthesis as defined by claim 6, wherein the elongated shaft (16) includes a rod element, and wherein balls (14, 14', 14") are provided with through bores through which they are slipped and then fixed on the rod element.

9. The ossicle prosthesis as defined by claim 7, wherein the balls (14, 14', 14") are welded to the rod element.

10. The ossicle prosthesis as defined by claim 7, wherein the through bores of the balls (14, 14', 14") are produced by means of lasers.

11. The ossicle prosthesis as defined by claim 7, wherein the rod element is made from a flexible material.

12. The ossicle prosthesis as defined by claim 1, wherein the securing elements (11, 12; 22) are embodied in forms selected from a group consisting of: plate-shaped, bell-shaped ram-shaped and a clip.

13. The ossicle prosthesis as defined by claim 1, wherein the first securing element (11) includes a head plate embodied for contact with the eardrum.

14. The ossicle prosthesis as defined by claim 1, wherein the prosthesis or parts thereof are made from material selected from a group consisting of: titanium, gold, tantalum, titanium alloy, gold alloy and tantalum alloy.

15. The ossicle prosthesis as defined by claim 1, wherein each of the two struts (13, 13') of the ball joint has a plurality of recesses (15, 15') that located side by side for receiving a ball (14) of the elongated shaft (16), and wherein two of the plurality of recesses (15 and 15') are arranged diametrically opposite one another.

16. The ossicle prosthesis as defined by claim 9, wherein balls (14, 14', 14") are welded to the rod element by means of laser welding.

* * * * *

(12) INTER PARTES REEXAMINATION CERTIFICATE (717th)
United States Patent
Steinhardt et al.

(10) Number: US 7,553,328 C1
(45) Certificate Issued: Oct. 28, 2013

(54) OSSICLE PROSTHESIS

(75) Inventors: Uwe Steinhardt, Hirrlingen (DE); Heinz Kurz, Dusslingen (DE)

(73) Assignee: Heinz Kurz GmbH Medizintechnik, Dusslingen (DE)

Reexamination Request:
No. 95/002,213, Sep. 13, 2012

Reexamination Certificate for:
Patent No.: 7,553,328
Issued: Jun. 30, 2009
Appl. No.: 10/579,927
Filed: May 19, 2006

(21) Appl. No.: 95/002,213
(22) PCT Filed: Dec. 7, 2005
(86) PCT No.: PCT/EP2005/013077
§ 371 (c)(1),
(2), (4) Date: May 19, 2006
(87) PCT Pub. No.: WO2006/094543
PCT Pub. Date: Sep. 14, 2006

(30) Foreign Application Priority Data

Mar. 9, 2005 (DE) .......................... 10 2005 010 705

(51) Int. Cl.
*A61F 2/18* (2006.01)

(52) U.S. Cl.
USPC ............................................................ 623/10

(58) Field of Classification Search
None
See application file for complete search history.

(56) References Cited

To view the complete listing of prior art documents cited during the proceeding for Reexamination Control Number 95/002,213, please refer to the USPTO's public Patent Application Information Retrieval (PAIR) system under the Display References tab.

*Primary Examiner* — David O. Reip

(57) ABSTRACT

An ossicle prosthesis (10) includes a first securing element (11) and a second securing element (12), the second securing element connected to a member of the ossicle chain. The ossicle chain ends at the first securing element in a ball joint, which includes two struts (13, 13') solidly connected to the first securing element (11). The two struts enclose a gaplike space, in which a ball (14) is pivotably supported in two recesses (15), the ball (14) being part of an elongated shaft (16) that connects the first and second securing elements and includes many balls (14, 14', 14") adjacent to one another. The elongated shaft is displaceable through the gaplike space between the two struts and through a perforation (17) in the first securing element, where one of the balls snaps between the respective recesses. The gaplike space can be made narrower between the two struts (13, 13') of the ball joint for fixation of the shaft (16) after the desired length has been adjusted.

INTER PARTES REEXAMINATION CERTIFICATE ISSUED UNDER 35 U.S.C. 316

NO AMENDMENTS HAVE BEEN MADE TO THE PATENT

AS A RESULT OF REEXAMINATION, IT HAS BEEN DETERMINED THAT:

The patentability of claims 1-16 is confirmed.

\* \* \* \* \*